United States Patent
Groll et al.

[11] Patent Number: 5,779,480
[45] Date of Patent: Jul. 14, 1998

[54] PROSTHETIC ABUTMENT FOR DENTAL IMPLANTS

[75] Inventors: Werner Groll, Alzenau; Thomas Lange, Langenselbold; Pascale Grote, Hanau; Willi Meiers, Alzenau, all of Germany

[73] Assignee: Degussa Aktiengesellschaft, Frankfurt am Main 1, Germany

[21] Appl. No.: 859,425

[22] Filed: May 20, 1997

[30] Foreign Application Priority Data

May 21, 1996 [DE] Germany ............ 196 20 394.5

[51] Int. Cl.$^6$ .................................................. A61C 8/00
[52] U.S. Cl. ........................................... 433/173; 433/172
[58] Field of Search ............................. 433/172, 173, 433/174

[56] References Cited

U.S. PATENT DOCUMENTS 5,376,004  12/1994  Mena ............................ 433/173
5,447,435   9/1995  Brodbeck ....................... 433/173
5,527,182   6/1996  Willoughby ..................... 433/172
5,571,016  11/1996  Ingber et al. ................... 433/173
5,674,069  10/1997  Osorio ........................... 433/172

*Primary Examiner*—John J. Wilson
*Attorney, Agent, or Firm*—Beveridge, DeGrandi, Weilacher & Young, LLP

[57] ABSTRACT

A prosthetic abutment made from metal for securing to the enossal part of a dental implant is capable of being adapted to the natural shape of the individual teeth inasmuch as it ends on the occlusal side in a truncated cone produced by removal of material from a paraboloid of revolution, said truncated cone having in cross-section a semi-elliptical base plane on the labial side and a paraboloid base plane on the lingual side.

2 Claims, 1 Drawing Sheet

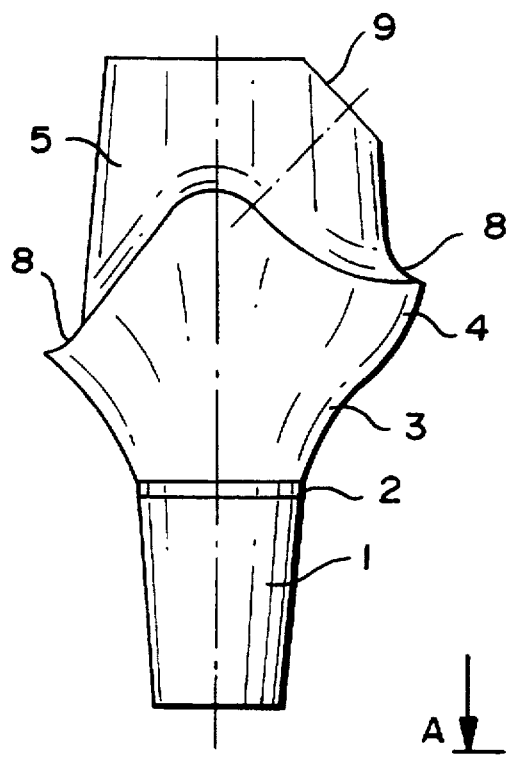
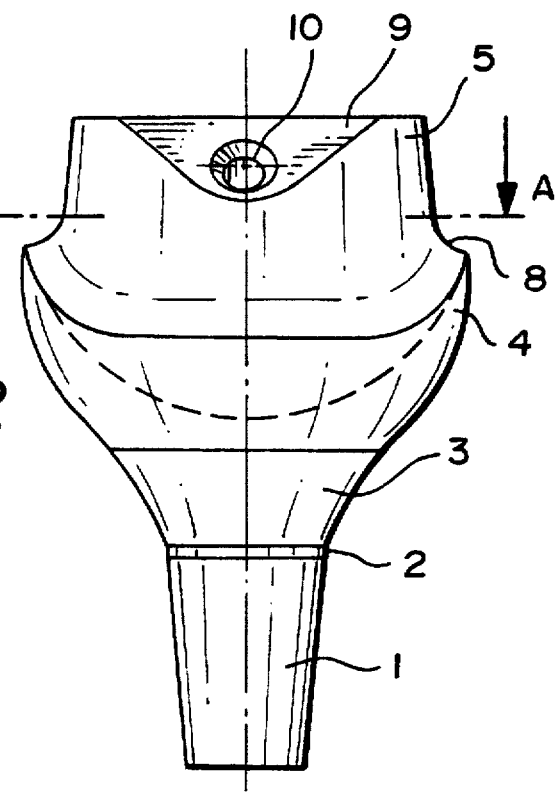
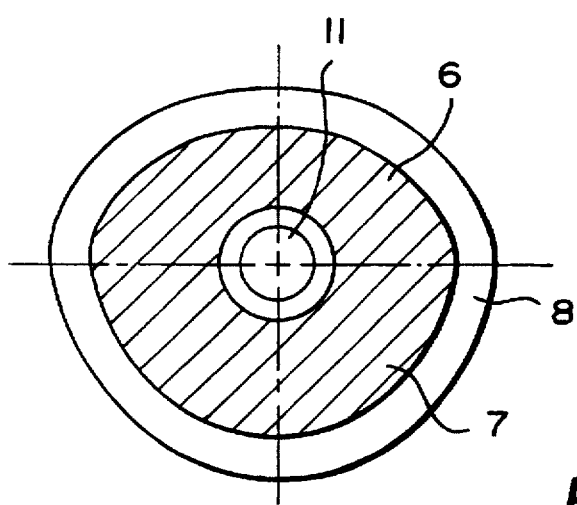

PROSTHETIC ABUTMENT FOR DENTAL IMPLANTS

INTRODUCTION AND BACKGROUND

The present invention relates to a prosthetic abutment made from metal for a two-phase dental implant, said abutment being secured with the aid of a central screw to the enossal part of the dental implant anchored in the jawbone and accommodating on the occlusal side a prosthetic device such as a crown or bridge.

The loss of natural teeth can be compensated in various ways by means of artificial prosthetic components. In recent years use has increasingly keen made of dental implants generally consisting of two metallic parts, one of which is anchored in the toothless jaw beneath the mucosa. Once this part has grown firmly into the bone, a second part, the so-called abutment, is screwed into the first part with a view to supporting dental prosthetic devices such as a crown or bridge. These abutment are prefabricated in relatively large numbers and supplied in standard designs.

Dental implants and mounting posts or abutments have been described in numerous publications. With all mounting posts, the part which passes through the gingiva into the oral cavity is circular in cross section. A natural tooth, on the other hand, has a cross-section which deviates to a greater or lesser extent from a circular shape, especially in the region of the anteriors.

The production of a prosthetic device resembling a tooth as closely as possible presupposes a considerable effort in terms of dental technology, but this usually entails hygienic problems when it comes to cleaning these costly prosthetic components.

Hence, the object of the present invention was to develop a prosthetic abutment made from metal for a two-phase dental implant, said abutment being secured with the aid of a central screw to the enossal part of the dental implant anchored in the jawbone and accommodating on the occlusal or top side the prosthetic device such as a crown or bridge and the cross-sectional shape of the mounting post in the region of the oral cavity being adapted as closely as possible to the shape of the natural teeth and lending itself readily to manufacturing by means of the currently available machine tools.

SUMMARY OF THE INVENTION

The above and other objects of the invention are achieved by forming that part of the mounting post which faces the enossal part of the dental implant in the form of a cone. The cone-shaped section is followed by a section configured as a hyperboloid of revolution opening out in the upward direction and passing in a further section into a stump configured as a paraboloid of revolution exhibiting on the occlusal side the shape of a truncated cone produced by removal of material. It is a feature of the invention that the truncated cone has in cross-section a semi-elliptical base plane on the labial side and a paraboloid base plane on the lingual side. As a result, the transition between the truncated cone and the stump configured as a paraboloid of revolution is situated in the region where the abutment passes through the gingiva and takes the form of a shoulder having a uniform width between 0.1 and 1.5 mm. It is further feature of the invention that the truncated cone tapers at an angle between 1° and 15° in the upward direction.

At its occlusal end, a part of the truncated cone is preferably bevelled at an angle of 30° to 600° in relation to the principal axis and provided with a borehole.

It is moreover advantageous for the abutment to be made from titanium or from a titanium alloy.

BRIEF DESCRIPTION OF THE DRAWINGS

The present invention will be further understood with reference to the drawings; wherein:

FIG. 1 is a schematic elevational view of the abutment according to the invention;

FIG. 2 is a schematic elevational View of the mounting post according to the invention rotated 180° C. from the view shown in FIG. 1; and FIG. 3 is a schematic cross sectional view taken through the plane A—A of FIG. 2.

DETAILED DESCRIPTION OF INVENTION

The shape of the truncated cone is, as far as possible, adapted to that of the natural teeth, especially since the cross-section can be varied. Material can be removed from the stump configured as a paraboloid of revolution preferably by milling with the aid of automatically controlled CNC machines. This removal of metal material is controlled in such a way as to ensure that by way of a transition between the truncated cone produced by machining and the paraboloid of revolution a shoulder is produced having a uniform width between 0.1 and 1.5 mm, the prosthetic component such as a bridge or crown being mounted on said shoulder. In view of the fact that, owing to the non-uniform cross-section of the truncated cone, material is removed to different depths, this shoulder is undulated in shape and therefore resembles a natural tooth also in this respect.

With reference to FIG. 1, the abutment of this invention consists of a lower most part (1) configured as a first truncated cone to be anchored to the portion of the dental implant that is fitted into the jaw bone, and opening out in the upward direction at an angle of 4° to 10° . By way of transition to section (3), a section which is configured as a hyperboloid of revolution, a short cylindrical section (2) is provided, which is, however, not absolutely essential, it being merely intended to facilitate manipulation. The hyperboloid of revolution passes in an unpaved direction into a section (4), the shape of which corresponds to that of a stump configured as a paraboloid of revolution and ends on the occlusal side in a second truncated cone (5) produced by removal of material. The top side or top end of the abutment is referred to as the "occlusal side" indicating that the crown, bridge or other artificial tooth is attached to that end.

The second truncated cone (5) as can be seen from the drawings is larger than the first cone (1) located at the lower most end, the enossal end, of the mounting post of this invention.

This truncated cone (5) has a cross-section as shown in FIG. 3 exhibiting on the labial side a semi-elliptical base plane (6) and on the lingual side a paraboloid base plane (7). The labial side of the large truncated cone (5) is the side that will face the lips when the abutment is anchored in position in the patient's mouth.

As shown in FIG. 2, by varying the axial ratio of the semi-ellipse it is possible to vary also the cross-section of the truncated cone (5) so as to adapt it to the particular shape of the individual natural teeth. The removal of material with a view to producing the truncated cone (5) is effected in such a way that the transition between the truncated cone (5) and the stump (4) configured as a paraboloid of revolution takes the form of a shoulder (8) of uniform width. Hence, inasmuch as the cross-section of the truncated cone (5) is only partly symmetrical, the shape of this shoulder is undulated. Preferably, a part (9) of the truncated cone (5) is bevelled at an angle of 30° to 60° in relation to the principal axis and provided with a borehole (10) in order to be able to bring about perfect attachment of the later installed prosthetic component to the mounting post. The mounting post is screwed to the enossal part of the implant via a central borehole (11) as shown in FIG. 3.

Further variations and modifications will be apparent to those skilled in the art and are intended to be encompassed by the claims appended hereto.

German priority application 196 20 394.5 is relied on and incorporated herein by reference.

We claim:

1. A prosthetic abutment made from metal for a two-phase dental implant, said abutment having a lower end for securing with the aid of a central screw to an enossal part of a dental implant anchored in a jawbone of a patient in need thereof and said abutment having an upper occlusal end for attachment to a prosthetic device, said abutment comprising a lower most part of the abutment for mating engagement with an enossal part of a dental implant in the form of a first truncated cone, said first truncated cone being followed by and attached to a section of the abutment configured as a hyperboloid of revolution opening out in an upward direction and passing in a further section into a stump configured as a paraboloid of revolution having on an occlusal side the shape of a second truncated cones, said second truncated cone having a larger cross-section than said first truncated cone and being of a semi-elliptical base plane in cross section on a labial side of said abutment and a paraboloid base plane on a lingual side of said abutment, whereby the transition between the truncated cone and the stump configured as a paraboloid of revolution is situated in the region where the abutment passes through the gingiva and takes the form of a shoulder having a uniform width between 0.1 and 1.5 mm and where the truncated cone tapers at an angle of 1° to 15° in the upward direction.

2. The prosthetic abutment according to claim 1, wherein a part of the second truncated cone is bevelled at an angle of 30° to 60° with respect to the principal axis at an occlusal side and being provided with a borehole.

* * * * *